Dec. 23, 1958 E. S. BOERNER Plant Pat. 1,784
ROSE PLANT
Filed April 28, 1958
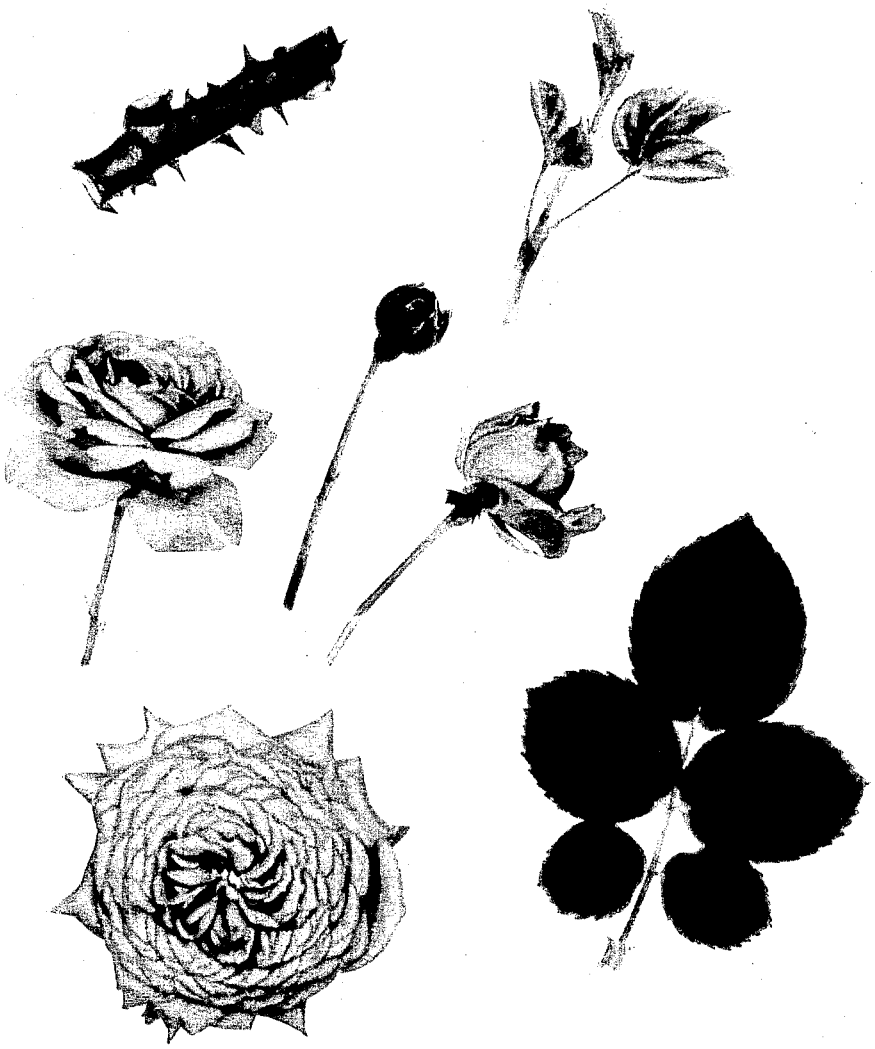
Inventor.
E. S. Boerner
By: Robb & Robb
Attorneys.

United States Patent Office

Plant Pat. 1,784
Patented Dec. 23, 1958

1,784

ROSE PLANT

Eugene S. Boerner, Newark, N. Y., assignor to Jackson & Perkins Company, Newark, N. Y., a corporation of New York Application April 28, 1958, Serial No. 731,558

1 Claim. (Cl. 47—61)

The present invention relates to a new and distinct variety of rose plant of the large-flowered polyantha class, which was originated by me by crossing the variety "Spice" (Plant Patent No. 1,396) with the variety "Garnette" (unpatented).

The primary objective of this breeding was a part of a more comprehensive program involving an attempt to improve the lasting quality of the flowers of various varieties of rose plants of different colors. In the present instance, the objective was more particularly concerned with roses falling in the range of red colors, and the objective was fully achieved, along with other improvements, as evidenced by the following unique combination of characteristics which are outstanding in the new variety and distinguish it from its parents as well as from all other varieties of which I am aware:

(1) A floriferousness which is unusual and makes the new variety especially adaptable for many uses;

(2) Fully double flowers, each having a large number of thick petals, yet opening gracefully;

(3) A distinctive Carmine, lightly overcast with Spectrum Red, general color tonality of the flowers;

(4) A retention of the flower color uniformly throughout the life of the flowers; and (5) A long-lasting flower quality comparable to that of the parent variety "Garnette."

Asexual reproduction of the new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Spice."
*Pollen parent.*—"Garnette."

Classification:
*Botanic.*—Large-flowered polyantha.
*Commercial.*—Floribunda.

*Flower*

(Observations made from specimens grown in a greenhouse at Newark, New York, in the early afternoon during the early part of March.)

Blooming habit: Recurrent—continuous.

Bud:
*Size.*—Medium.
*Form.*—Short, with flat top; is not affected by wet or hot weather.

*Color.*—When sepals first divide—Victoria Lake, Plate 1. When petals begin to unfurl—Oxblood Red, Plate 1. When half-blown: inside of petals—Carmine, Plate 1; reverse of petals—Carmine, Plate 1, lightly overcast with Spectrum Red, Plate 1.
*Sepals.*—Slightly branched; curl back when petals begin to unfurl. Color: inside—Biscay Green, Plate 17; outside—Forest Green, Plate 17.
*Calyx.*—Color—Forest Green, Plate 17. Shape—pear. Size—small. Aspect—smooth. Odor when rubbed—none.
*Peduncle* — Length — short. Aspect — smooth. Strength—erect; slender. Color—Light Bice Green, Plate 17.
*Opening.*—Opens up well; is not affected by adverse weather conditions.

Bloom:
*Size.*—Medium. Average size when fully expanded—from 2 inches to 2½ inches.
*Borne.*—Both singly and several together.
*Stems.*—Medium length; strong.
*Form (when first open).*—Cupped. Permanence—retains its form to the end, but outer petals curl back.
*Petalage.*—Very double; many petals and stamens hidden. Number of petals under normal conditions—from 80 to 85.
*Color.*—Center of flower—Spectrum Red, Plate 1. Outer petals—Carmine, Plate 1. Base of petals (aiglet)—White, Plate 53. Inside of petals—Carmine, Plate 1, lightly overcast with Spectrum Red, Plate 1. Reverse of petals—Carmine, Plate 1, lightly overcast with Pomegranate Purple, Plate 12. General tonality from a distance—Spectrum Red, Plate 1.
*Discoloration*—General tonality at end of first day—Carmine, Plate 1. Second day—Carmine, Plate 1, lightly overcast with Spectrum Red, Plate 1. Third day—Carmine, Plate 1, lightly overcast with Spectrum Red, Plate 1.

Petals:
*Texture.*—Thick; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—None.
*Persistence.*—Hang on and dry.
*Fragrance.*—Moderate. Nature—tea (average hybrid tea scent).
*Lasting quality.*—On the plant—very long. As cut flower—very long.

*Genital organs*

Stamens, Anthers: Small; few; regularly arranged around styles. Color—Cadmium Yellow, Plate 3.
Stamens, filaments (threads): Medium length. Color—Capucine Buff, Plate 3.
Pollen: Color—Pale Yellow-Orange, Plate 3.
Styles: Loosely separated; medium length; thin.
Stigmas: Color—Pale Chalcedony Yellow, Plate 17.
Ovaries: All enclosed in calyx.
Hips: None.
Seeds: None.

*Plant*

Form: Bush.
Growth: Medium; upright; branching.
Foliage: Compound of 5 to 7 leaflets.
*Size.*—Medium.
*Quantity.*—Normal.

*Color.*—New foliage: upper side—Garnet Brown, Plate 1; under side—Brazil Red, Plate 1. Old foliage: upper side—Dark Dull Yellow-Green, Plate 3; under side—Bice Green, Plate 17.

*Shape.*—Oval pointed.

*Texture.* — Upper side — leathery. Under side—smooth.

*Ribs and veins.*—Ordinary.

*Edge.*—Serrated (saw-toothed).

*Serration.*—Both double and single; small.

*Leaf stem.*—*Color*—Chromium Green, Plate 32. Under side—prickly.

*Stipules.*—Short; bearded.

Wood:

*New wood.*—Color—Rinnemann's Green, Plate 17. Bark—smooth.

*Old wood.*—Color—Cedar Green, Plate 6. Bark—smooth.

Thorns:

*Thorns.*—Quantity: on main stalks from base—ordinary; on laterals from stalk—ordinary. Form— narrow base; medium length; straight. Color (when young)—Begonia Rose, Plate 1. Position—irregular.

*Prickles.*—Quantity: on main stalks from base—none; on laterals from stalk—none.

*Short needles.*—Quantity: on main stalks from base—none; on laterals from stalk—none.

I claim:

A new and distinct variety of rose plant of the large-flowered polyantha class, substantially as herein shown and described, characterized particularly as to novelty by the unique combination of unusual floriferousness, fully double flowers, each having a large number of thick petals which open gracefully, a distinctive Carmine, lightly overcast with Spectrum Red, general color tonality of the flowers, a constant color retention throughout the life of the flowers, and an exceptionally good long-lasting quality of the flowers.

No references cited.